(12) United States Patent
Matsumoto

(10) Patent No.: US 10,987,439 B2
(45) Date of Patent: Apr. 27, 2021

(54) STERILIZATION METHOD AND STERILIZATION DEVICE

(71) Applicant: ASAHI KASEI KABUSHIKI KAISHA, Tokyo (JP)

(72) Inventor: Osamu Matsumoto, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 136 days.

(21) Appl. No.: 16/140,874

(22) Filed: Sep. 25, 2018

(65) Prior Publication Data

US 2019/0091357 A1    Mar. 28, 2019

(30) Foreign Application Priority Data

Sep. 26, 2017 (JP) .............................. JP2017-185430
Sep. 10, 2018 (JP) .............................. JP2018-168467

(51) Int. Cl.
*A61L 2/10* (2006.01)
*A61L 2/24* (2006.01)

(52) U.S. Cl.
CPC ................... *A61L 2/10* (2013.01); *A61L 2/24* (2013.01); *A61L 2202/23* (2013.01)

(58) Field of Classification Search
CPC ........... A61L 2/10; A61L 2/24; A61L 2202/23
See application file for complete search history.

(56) References Cited

U.S. PATENT DOCUMENTS

2014/0202948 A1    7/2014    Li

FOREIGN PATENT DOCUMENTS

| EP | 2805912 A1 | 11/2014 |
| JP | 2006-116536 A | 5/2006 |
| JP | 4494540 B2 | 6/2006 |
| JP | 6166441 B | 6/2017 |

OTHER PUBLICATIONS

Supplementary European Search Report corresponding to European Patent Application No. 18196518.7 dated Feb. 21, 2019, 4 pages.
European Search Report for European Application No. 18196518.7, dated Mar. 5, 2021, 9 pages.

*Primary Examiner* — Sean E Conley
(74) *Attorney, Agent, or Firm* — Morgan, Lewis & Bockius LLP

(57) ABSTRACT

There are provided a sterilization method and a sterilization device capable of effectively sterilizing a sterilization target having an uneven shape formed by a dented portion and a protruded portion. A sterilization method and a sterilization device configured to apply ultraviolet light to a sterilization target having an uneven shape formed by a dented portion and a protruded portion include plural light sources each including an LED element configured to apply ultraviolet light. Ultraviolet light is simultaneously applied from each of the plural LED elements in a state where the sterilization target arranged at previously set irradiation positions face the plural light sources, and reaches the sterilization target.

14 Claims, 10 Drawing Sheets

STERILIZATION METHOD AND STERILIZATION DEVICE

CROSS REFERENCE TO RELATED APPLICATIONS AND INCORPORATION BY REFERENCE

This application claims benefit of priority under 35 USC 119 based on Japanese Patent Applications Nos. 2017-185430 filed on Sep. 26, 2017 and 2018-168467 filed on Sep. 10, 2018, the entire contents of which are incorporated by reference herein.

TECHNICAL FIELD

The present invention relates to a sterilization method and a sterilization device for use in sterilization of, for example, food-accommodating containers.

BACKGROUND ART

As an example of technologies for sterilizing a sterilization target (such as a container) by ultraviolet light, there is an ultraviolet light irradiation technology using a mercury lamp, as disclosed in JP 2006-116536 A.

SUMMARY

According to an aspect of invention, there is provided a sterilization method configured to apply ultraviolet light to a sterilization target having an uneven shape formed by a dented portion and a protruded portion from each of a plurality of light sources each including an LED element. The sterilization method includes: transferring the sterilization target; positioning the sterilization target; and irradiating the sterilization target with ultraviolet light. In the positioning, the sterilization target is stopped at a position in which ultraviolet light is emitted from the plurality of light sources. In the irradiating, the sterilization target is irradiated a plurality of times with the ultraviolet light from at least one of the light sources arranged at a position where irradiation intensity to the dented portion is maximum. According to another aspect of invention, there is provided a sterilization device configured to apply ultraviolet light to a sterilization target having an uneven shape formed by a dented portion and a protruded portion. The sterilization device includes a plurality of light sources configured to apply the ultraviolet light, each light source including an LED element configured to apply ultraviolet light. The ultraviolet light is simultaneously applied from each of the plurality of LED elements in a state where the sterilization target arranged at a previously set irradiation position face the plurality of light sources, and reaches the sterilization target.

DETAILED DESCRIPTION

Figure 1:
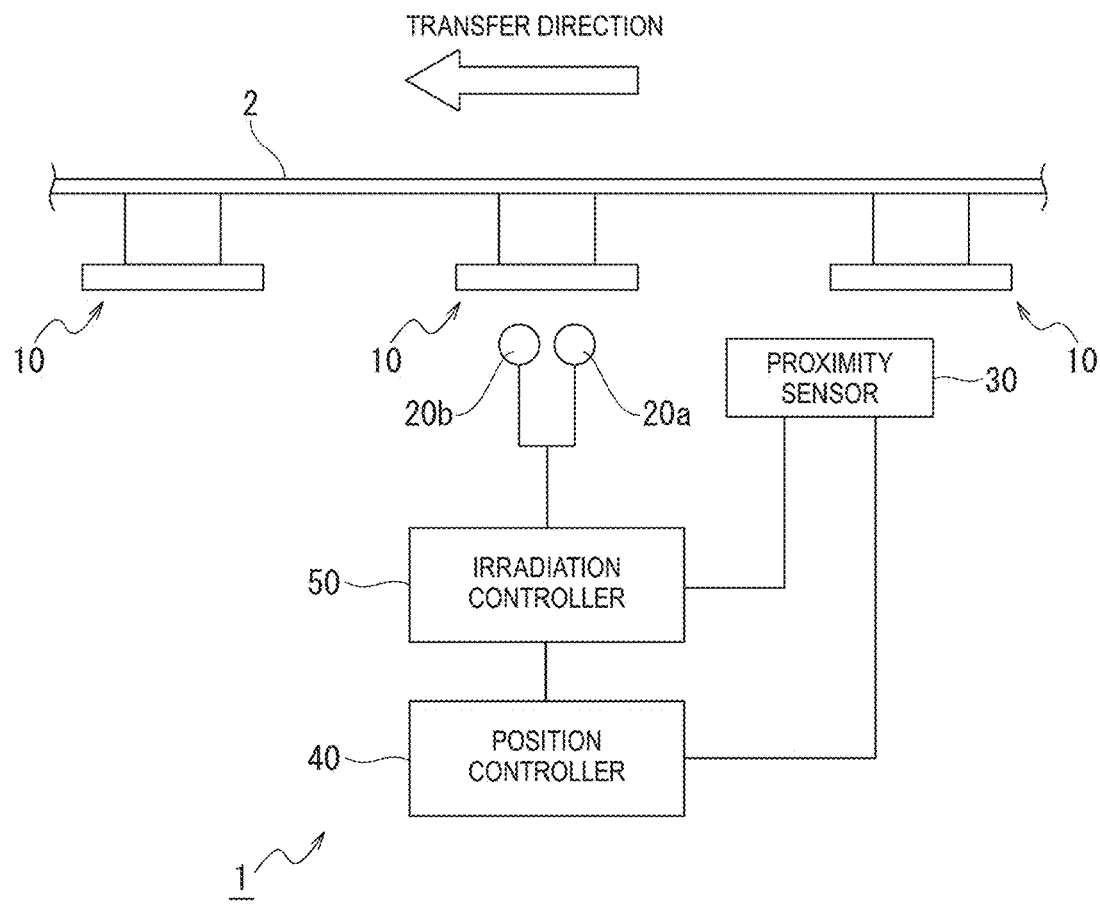
FIG. 1 is a diagram illustrating the schematic structure of a sterilization device according to a first embodiment of the present invention.

Mercury lamps are used by continuously keeping them on, because repeatedly turning a mercury lamp on and off shortens the lifetime of the lamp. However, ultraviolet light is necessary to be irradiated only when sterilization is desired. Thus, continuous lighting is a waste of power consumption. Additionally, long-hour ultraviolet irradiation can deteriorate resin or the like present around the device.

Accordingly, as in the technology described in JP 2006-116536 A, regarding a structure for irradiating with ultraviolet light using a mercury lamp, a technology for providing a shutter mechanism has been proposed to allow a mercury lamp to irradiate a sterilization target with ultraviolet light only during transfer of the sterilization target. However, applying the technology for providing a shutter mechanism complicates the shape and manufacturing of the device.

The above problem is solved by using an LED instead of a mercury lamp to irradiate with ultraviolet light, since there is no need for providing a shutter mechanism, so that the shape and manufacturing of the device can be simplified.

However, in the case of a sterilization target having an uneven shape formed by a dented portion and a protruded portion, even when ultraviolet light irradiation is performed using an LED, the ultraviolet light is not sufficiently applied to a shaded region formed by the protruded portion. Due to this, a problem arises where sterilization is insufficient.

Embodiments described below have been accomplished by focusing on the conventional unsolved problems, and it is an object of the embodiments to provide a sterilization method and a sterilization device capable of effectively sterilizing a sterilization target having an uneven shape.

Embodiments of the present invention will be described below with reference to the drawings. In the description of the drawings referred to in the following description, the same or similar parts are denoted by the same or similar reference signs. The drawings are schematic representation, and therefore it should be noted that the relationships between thickness and planar dimensions, thickness ratios, and the like are different from actual ones. Accordingly, specific thicknesses and dimensions are should be determined in consideration of the following description. It is also obvious that there are some differences in dimensional relationships and ratios between the mutual drawings.

In addition, the embodiments given below exemplify structures for embodying the technological ideas of the present invention, and the technological ideas of the invention should not be construed as specifying the materials, shapes, configurations, arrangements, and the like of the components to those given below. Various modifications can be added to the technological ideas of the present invention within the technological scope of the claims. Furthermore, in the following description, the directions of "left and right" and "up and down" are simply defined for only convenience of explanation, and do not limit the technological ideas of the present invention. Therefore, it is obvious that, for example, when a paper plane is rotated at 90 degrees, the "left and right" direction and the "up and down" direction are read by switching, whereas when the paper plane is rotated at 180 degrees, the "left" turns to the "right" and the "right" to the "left".

First Embodiment

Hereinafter, a first embodiment of the present invention will be described with reference to the drawings.
(Structure)
The structure of the first embodiment will be described using FIG. 1 to FIG. 3.

A sterilization device 1 illustrated in FIG. 1 is a device configured to apply ultraviolet light to a sterilization target 10 transferred by being placed on a moving unit 2 (a belt) included in a transfer apparatus (for example, a belt conveyor). Note that FIG. 1 illustrates a positional relationship between the moving unit 2 and the sterilization target 10, as a schematic relationship.

First Embodiment

Additionally, the sterilization device 1 includes a plurality of light sources 20, a proximity sensor 30, a position controller 40, and an irradiation controller 50.

In the first embodiment, as one example, a case where the sterilization device 1 includes two light sources 20a and 20b will be described. Note that, in the drawings and in the description hereinbelow, the light source 20 arranged upstream in a direction in which the sterilization target 10 is transferred (indicated as "TRANSFER DIRECTION" in FIG. 1) is defined as light source 20a, and the light source 20 arranged downstream in the transfer direction is defined as light source 20b.

Figure 2:
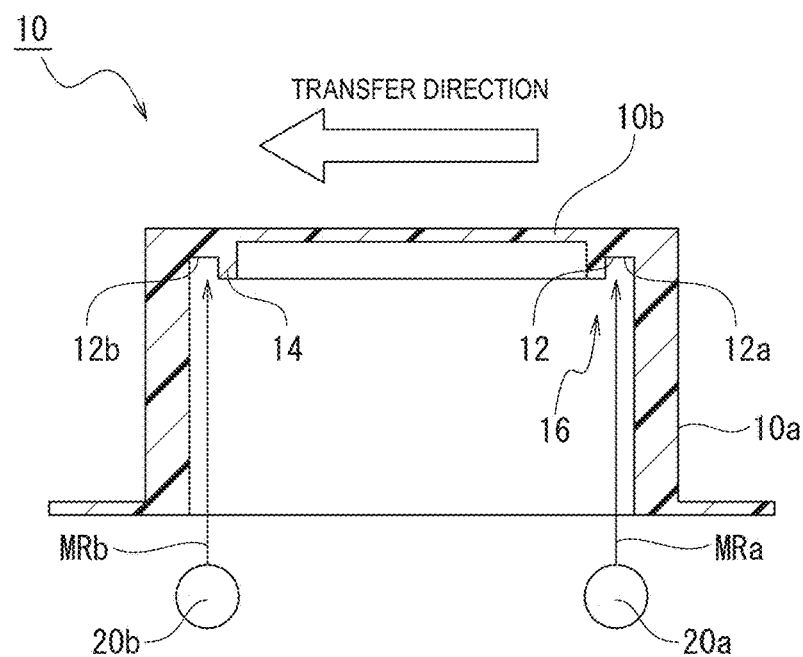
FIG. 2 is a diagram illustrating directions of ultraviolet light applied to a sterilization target.

The sterilization target 10 has an uneven shape 16 formed by a dented portion 12 and a protruded portion 14, as illustrated in FIG. 2. Accordingly, the sterilization device 1 is a device configured to apply ultraviolet light to the sterilization target 10 having the uneven shape 16 formed by the dented portion 12 and the protruded portion 14. Note that FIG. 2 illustrates a cross-sectional diagram of the sterilization target 10 taken along a center line in the transfer direction.

In the first embodiment, as one example, a case where the sterilization target 10 is a cap configured to close the opening portion of a container for accommodating an article will be described.

Examples of the caps include lids of containers (such as glass bottles) for accommodating seasoning powder and caps of containers (plastic bottles) for accommodating drinking water.

A description will be given of a case where the cap is a cylindrical member including a cylindrical portion 10a and a bottom face portion 10b. One end of the cylindrical portion 10a formed into a cylindrical shape is closed by the bottom face portion 10b having a plate-like shape, and the other end of the cylindrical portion 10a is open.

Accordingly, the dented portion 12 and the protruded portion 14 are formed on the bottom face portion 10b (a bottom face of the sterilization target 10).

The protruded portion 14 is an annular protrusion formed at a position spaced by a gap from an inner diameter surface of the cylindrical portion 10a on the bottom face portion 10b.

The dented portion 12 is an annular groove formed between the inner diameter surface of the cylindrical portion 10a and the protruded portion 14 on the bottom face portion 10b.
(Light Source)
Each light source 20 applies ultraviolet light.

In the first embodiment, as one example, a case where the ultraviolet light that is applied by the light source 20 is ultraviolet C wave (UVC) will be described.

Each of the light sources 20a and 20b includes an LED element (not illustrated) that can apply ultraviolet light and is capable of emitting light to at least a main emission direction.

Figure 3:
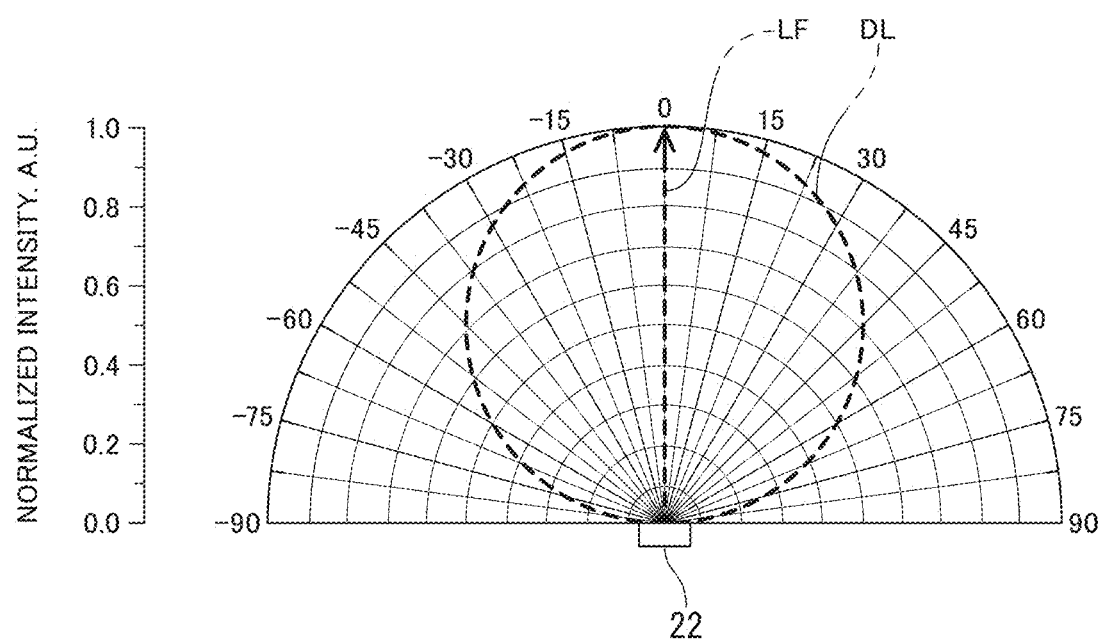
FIG. 3 is an illumination distribution chart representing a relationship between intensity and direction of light emitted by an LED element.

Intensity of light emitted from the LED element 22 is defined by, for example, a relationship between the intensity and direction of the light emitted from the LED element 22, as illustrated in FIG. 3. Note that FIG. 3 is an illumination distribution chart representing the relationship between the intensity and direction (angle) of light emitted from the LED element 22. Additionally, in FIG. 3, the outline of a region representing the distribution of illumination is indicated by a dotted line DL. Furthermore, in FIG. 3, the vertical axis represents the intensity of light emitted from the LED element 22 by describing as "NORMALIZED INTENSITY. A.U".

Note that examples of the "intensity of light" include brightness, illumination, luminous flux, and luminous intensity.

In the example illustrated in FIG. 3, most intensely emitted light is light emitted in a direction vertical (0 degrees) to the LED element 22. Note that, in FIG. 3, light emitted vertically to the LED element 22 is represented by an arrow LF.

A main emission direction MRa of the LED element included in the light source 20a and a main emission direction MRb of the LED element included in the light source 20b are directed toward different positions on the sterilization target 10 arranged at an irradiation position, which is a previously set position. In other words, the LED element of at least one (the light source 20a) of the plurality of light sources 20 and the LED element of the other one (the light source 20b) of the plurality thereof are mutually different in terms of the direction of ultraviolet light irradiation. Note that the "irradiation position" will be described later.

Additionally, the expression "mutually different in terms of the direction of ultraviolet light irradiation" means a state where when ultraviolet light is applied simultaneously from the plurality of light sources (the light sources 20a and 20b) in a state where the sterilization target 10 arranged at a previously set irradiation position opposes (faces) the plurality of light sources 20, the main emission directions of ultraviolet light emitted from the plurality of light sources reach different positions on the sterilization target 10.

Accordingly, the expression "mutually different in terms of the direction of ultraviolet light irradiation" includes a state where even when vectors of ultraviolet light applied from the plurality of light sources are the same and the main emission directions of the ultraviolet light applied from the plurality of light sources are parallel to each other, the main emission directions of the ultraviolet light applied from the plurality of light sources reach different positions on the sterilization target 10.

Specifically, as illustrated in FIG. 2, the main emission direction MRa is directed toward a first irradiation position 12a that is a portion located at an upstream side of the transfer direction on the dented portion 12 forming the uneven shape 16. In addition to this, the main emission direction MRb is directed toward a second irradiation position 12b that is a portion located at a downstream side of the transfer direction on the dented portion 12 forming the uneven shape 16.

In other words, the main emission direction MR of the LED element included in at least one (the light source 20a, 20b) of the light sources 20 is directed toward the dented portion 12.

Note that since the sterilization target 10 is the cylindrical cap, the first irradiation position 12a and the second irradiation position 12b indicate different positions on the dented portion 12 having the same structure.

Additionally, the plurality of light sources 20 are arranged to be equidistantly spaced apart from each other along a perfect circle (along a virtual perfect circle) opposing the annular dented portion 12. In other words, the first irradiation position 12a and the second irradiation position 12b are arranged at an equal interval (a 180 degree interval) along a circumferential direction of the dented portion 12 in the dented portion 12 formed into the cylindrical shape.

Accordingly, the LED elements 22 included in the plurality of light sources 20 provided in an irradiation unit are respectively arranged on a circumference of the virtual perfect circle opposing the sterilization target 10.

Thus, ultraviolet light is applied simultaneously from each of the plurality of LED elements in the state where the sterilization target 10 arranged in the previously set irradiation position faces the plurality of the light sources 20, and reaches the different positions on the sterilization target 10.

Additionally, at least one of the LED elements 22 included in the plurality of light sources 20 is arranged so as to apply ultraviolet light by directing the direction of a light beam with maximum light intensity toward the dented portion 12.

When the time of ultraviolet light irradiation by the light sources 20 is defined as "t", and the logarithmic reduction value per unit time is defined as "LRV", the logarithmic reduction value LRV is generally proportional to the irradiation time t. Therefore, when the sterilization efficiency of the light sources 20 is defined as "α", the sterilization efficiency α in a certain time domain seems to be theoretically constant.

However, the number of the LED elements forming the light sources 20 and the sterilization efficiency α are not always proportional. Even if the number of the LED elements forming the light sources 20 is set to twice, the sterilization efficiency α in a certain time is often not twice.

Thus, for example, when the sterilization effect of the light sources 20 is desired to be twice, the objective can be achieved by making the irradiation time twice. However, when the irradiation time is not changed, the number of the LED elements forming the light sources 20 needs to be twice or more.

Additionally, in a limited area, the smaller the number of LED elements with high output arranged, the further the reduction in dissipation of heat from the LED elements can be suppressed, so that reduction in LED output due to increased junction temperatures of the LED elements can be suppressed.

(Proximity Sensor)

The proximity sensor 30 is formed using, for example, a laser radar, a millimeter-wave radar, or the like, and detects the presence of the sterilization target 10 in a region set in the direction of the moving unit 2. After detecting the presence of the sterilization target 10, the proximity sensor 30 outputs an information signal indicating that the presence of the sterilization target 10 has been detected (which signal may be hereinafter referred to as "target detection signal" in the description hereinbelow) to the position controller 40 and the irradiation controller 50.

(Position Controller)

The position controller 40 includes, for example, a CPU, a RAM, and a ROM, and controls operation of the moving unit 2.

In addition, upon receipt of a target detection signal input from the proximity sensor 30, the position controller 40 stops the operation of the moving unit 2 so that the sterilization target 10 is positioned at an irradiation position.

Herein, the "irradiation position" is a position in which the main emission direction MRa is directed toward the first irradiation position 12a, and the main emission direction MRb is directed toward the second irradiation position 12b. The time during which the operation of the moving unit 2 is stopped is set according to, for example, output of the light sources 20, the shape and material of the sterilization target 10, and the like.

After stopping the operation of the moving unit 2, the position controller 40 outputs an information signal indicating that it has stopped the operation of the moving unit 2 (which signal may be hereinafter referred to as "transfer stop signal" in the description hereinbelow) to the irradiation controller 50.

(Irradiation Controller)

The irradiation controller 50 includes, for example, a CPU, a RAM, and a ROM, and controls operation of the light sources 20.

In addition, when the irradiation controller 50 receives a transfer stop signal input from the position controller 40 after receiving a target detection signal input from the proximity sensor 30, it allows the light sources 20a and 20b to apply ultraviolet C wave. The time for the ultraviolet C wave irradiation is set according to, for example, output of the light sources 20, the shape and material of the sterilization target 10, and the like.

In the first embodiment, as one example, a case where ultraviolet C wave is applied simultaneously from the light sources 20a and 20b will be described.

(Sterilization Method)

With reference to FIG. 1 and FIG. 2 and using FIG. 6, a description will be given of a sterilization method for sterilizing the sterilization target 10, which method is performed using the sterilization device 1 of the first embodiment.

The sterilization method is a sterilization method configured to apply ultraviolet light to the sterilization target 10 having the uneven shape 16 formed by the dented portion 12 and the protruded portion 14 from each of the plurality of light sources 20 each including the LED element.

Figure 6:
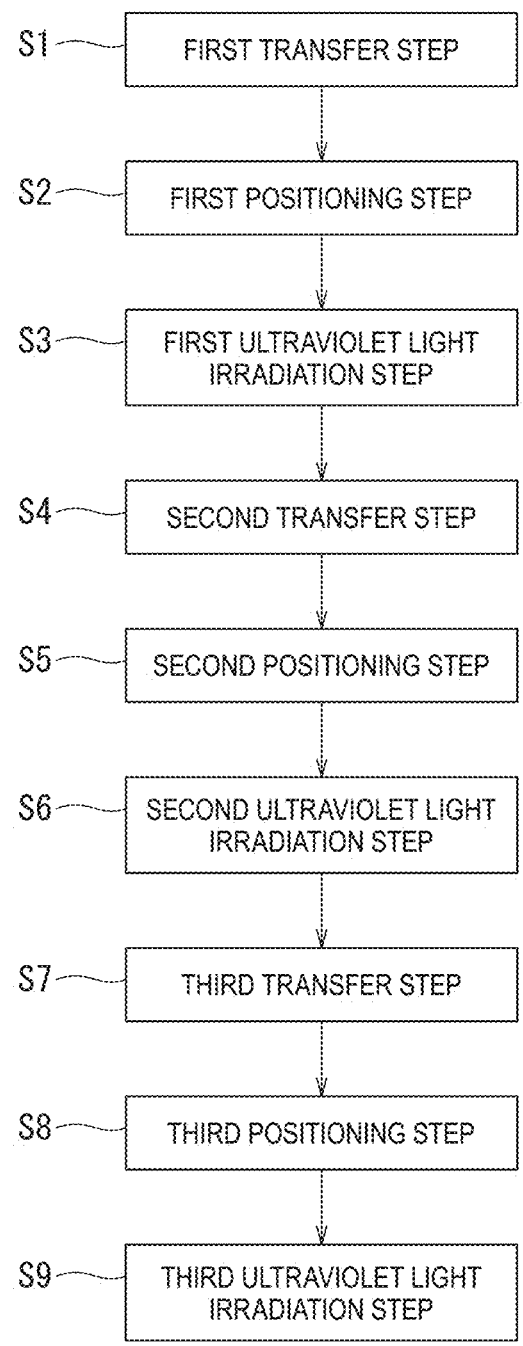
FIG. 6 is a flowchart representing a sterilization method.

Additionally, as illustrated in FIG. 6, the sterilization method includes a plurality of transfer steps, a plurality of positioning steps, and a plurality of ultraviolet light irradiation steps. Note that in the first embodiment, as one example, a case where the sterilization method includes three times of transfer steps, three times of positioning steps, and three times of ultraviolet light irradiation steps will be described, as illustrated in FIG. 6.

(Transfer Step)

The transfer step is a step of transferring the sterilization target 10 placed on the moving unit 2 to a region where ultraviolet C wave can be applied from the light sources 20.

Note that a second transfer step (step S4), which is a second-time transfer step, is performed as a post-step after a first ultraviolet light irradiation step (step S3), which is a first-time ultraviolet light irradiation step, as illustrated in FIG. 6. Similarly, a third transfer step (step S7), which is a third-time transfer step, is performed as a post-step after a second ultraviolet light irradiation step (step S6), which is a second-time ultraviolet light irradiation step.

(Positioning Step)

The positioning step is a step of arranging the sterilization target 10 transferred by being placed on the moving unit 2 at an irradiation position to which ultraviolet light is emitted from the plurality of light sources 20.

Thus, at the positioning step, the sterilization target 10 is arranged at a position in which the main emission direction MRa is directed toward the first irradiation position 12a, and the main emission direction MRb is directed toward the second irradiation position 12b.

In addition, at the positioning step, the sterilization target 10 is stopped at a position in which an average dose to a bottom region of the dented portion 12 is 0.1 mJ/cm$^2$ or more, and preferably 5 mJ/cm$^2$ or more when ultraviolet light is applied for one second from the LED elements 22 included in the plurality of light sources 20 provided in the irradiation unit.

(Ultraviolet Light Irradiation Step)

The ultraviolet light irradiation step is a step of irradiating ultraviolet light to the sterilization target 10 from the plurality of light sources 20.

At the ultraviolet light irradiation step, ultraviolet light is applied to the sterilization target 10 from each of the plurality of light sources 20 each including the LED element.

Specifically, at the ultraviolet light irradiation step, the main emission direction MRa of the LED element included in at least one (the light source 20a) of the plurality of light sources 20 and the main emission direction MRb of the LED element included in the other one (the light source 20b) of the plurality of light sources 20 are directed toward different positions on the sterilization target 10. Furthermore, ultraviolet light is applied to the different positions on the sterilization target 10 arranged at the irradiation position, simultaneously from the light source 20a and the light source 20b.

As a result, at the ultraviolet light irradiation step, ultraviolet light is applied to the different positions on the sterilization target 10 from the LED element included in at least one (light source 20a) of the plurality of light sources 20 and the LED element included in the other one (light source 20b) of the plurality of light sources 20.

In addition to this, at the ultraviolet light irradiation step, the main emission direction MRa is directed toward the first irradiation position 12a, and the main emission direction MRb is directed toward the second irradiation position 12b. Then, in this state, ultraviolet light is applied from the LED element of the light source 20a and the LED element of the light source 20b.

By doing this, at the ultraviolet light irradiation step, ultraviolet light is applied from at least one light source 20 arranged at a position where irradiation intensity to the dented portion 12 of the sterilization target 10 is maximum. Additionally, at the ultraviolet light irradiation step, ultraviolet light is applied to the dented portion 12 a plurality of times from the plurality of light sources 20.

Furthermore, at the ultraviolet light irradiation step, ultraviolet light is applied a plurality of times from at least one of the LED elements 22 included in the plurality of light sources 20 by directing the direction of a light beam with maximum light intensity toward the dented portion 12.

Additionally, at the ultraviolet light irradiation step, the plurality of times of ultraviolet light irradiation is performed at the plurality of different positions.

In addition, at the ultraviolet light irradiation step, ultraviolet light is applied to the different positions (the first irradiation position 12a and the second irradiation position 12b) of the sterilization target 10 from the LED element 22 included in at least one of the plurality of light sources 20 and the LED element 22 included in the other one of the plurality of light sources 20.

(Operation and Effects)

With reference to FIG. 1 and FIG. 2 and using FIG. 4 and FIG. 5, a description will be given of operation and effects of the first embodiment.

When sterilizing the sterilization target 10 using the sterilization device 1, the sterilization target 10 transferred by being placed on the moving unit 2 is arranged at the irradiation position, followed by ultraviolet light irradiation from the light sources 20a and 20b.

As described above, on the bottom face of the sterilization target 10 are formed the dented portion 12 and the protruded portion 14.

Figure 4:
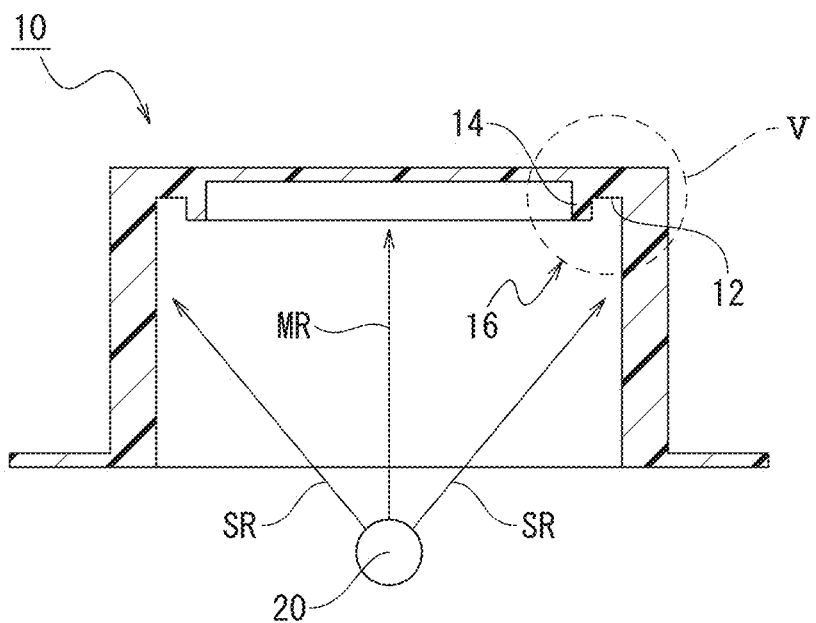
FIG. 4 is a diagram illustrating directions of ultraviolet light applied to a sterilization target in a sterilization device including a conventional structure.

Thus, in the configuration of a sterilization device including a conventional structure, i.e., for example, in a configuration in which the sterilization target 10 is sterilized by ultraviolet light applied only from a single light source 20, as illustrated in FIG. 4, the following problems arise. Note that, in FIG. 4, the main emission direction of an LED element included in the single light source 20 is indicated by a sign "MR". Similarly, the emission direction of light emitted in directions other than the main emission direction MR from the LED element included in the single light source 20 is indicated by a sign "SR". Additionally, note that, as in FIG. 2, FIG. 4 illustrates a cross-sectional diagram of the sterilization target 10 taken along the center line in the transfer direction.

Figure 5:
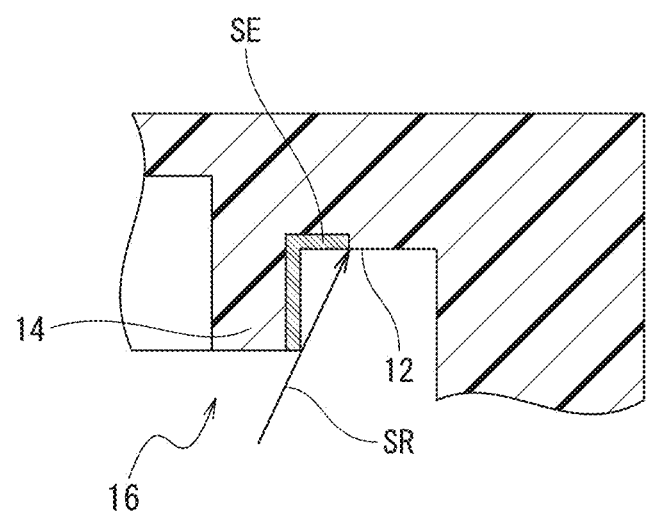
FIG. 5 is an enlarged view of a range enclosed by a circle V in FIG. 4.

In other words, as illustrated in FIG. 5, in the sterilization device including the conventional structure, there occurs a region to which ultraviolet light from the light source 20 is hardly applied due to being shaded by a wall formed by the protruded portion 14. Note that, in FIG. 5, the emission direction of light emitted in directions other than the main emission direction MR from the LED element included in the single light source 20 is indicated by a sign "SR". Additionally, in FIG. 5, the region shaded by the wall formed by the protruded portion 14 is indicated by a sign "SE".

Accordingly, in the sterilization device including the conventional structure, ultraviolet light is not sufficiently applied to the shaded region SE formed by the protruded portion 14, thus causing problems where sterilization is insufficient and sterilization takes time. By contrast, in the sterilization device 1 of the first embodiment, the main emission direction MRa of the LED element included in the light source 20a and the main emission direction MRb of the LED element included in the light source 20b are directed toward the different positions on the sterilization target 10.

Thus, the sterilization device 1 of the first embodiment enables ultraviolet light to be efficiently applied to the shaded region SE formed by the protruded portion 14, so that sterilization efficiency can be improved as compared with the sterilization device including the conventional structure. In addition, time required for sterilization can be shortened.

Note that the above-described first embodiment is one example of the present invention, and the invention is not limited thereto. Even in embodiments other than the present embodiment, various modifications can be made depending on design and the like without departing from the scope of the technological ideas of the present invention.

Effects of First Embodiment

The sterilization method of the first embodiment can provide effects described below.

(1) At the positioning step, the sterilization target 10 is stopped at the position where ultraviolet light is emitted from the plurality of light sources 20. Additionally, at the ultraviolet light irradiation step, ultraviolet light is applied to the sterilization target 10 a plurality of times from at least one light source 20 arranged at the position where the irradiation intensity to the dented portion 12 is maximum.

Thus, ultraviolet light can be efficiently applied to the dented portion 12 of the sterilization target 10, thus enabling improvement in sterilization efficiency.

As a result, there can be provided a sterilization method capable of effectively sterilizing the sterilization target 10 having the uneven shape 16.

In addition to this, since the time required for sterilization can be shortened, power consumption can be reduced, and also the lifetime of the LED elements can be extended. Additionally, heat generated from the LED elements can be reduced.

(2) A plurality of irradiation units each including the plurality of light sources 20 are arranged in the transfer direction of the sterilization target 10. Then, the transfer step, the positioning step, and the ultraviolet light irradiation step, respectively, are performed the plurality of times. Furthermore, the plurality of times of ultraviolet light irradiation is performed at the plurality of different positions.

As a result, variation in an ultraviolet light dose to the bottom face portion 10b and the uneven shape 16 can be suppressed, thus enabling the sterilization target 10 having the uneven shape 16 to be effectively sterilized.

(3) The LED elements 22 included in the plurality of light sources 20 provided in each of the irradiation units are respectively arranged on the circumference of the virtual perfect circle facing the sterilization target 10.

Thus, as compared with when ultraviolet light is applied to the single sterilization target 10 simultaneously from all the light sources 20 included in the single irradiation unit, the number of the light sources 20 for applying ultraviolet light to the single sterilization target 10 can be reduced.

As a result, the output of the light sources 20 can be efficiently applied to the dented portion 12.

In addition, since ultraviolet light can be applied in the multiple stages to a region where light beams emitted in directions other than the main emission direction MR from each light source 20 overlap with each other, the time of ultraviolet light irradiation can be increased without increasing the amount of energy consumption. Furthermore, the structure of a heat dissipation device included in each of the light sources 20 can be simplified.

(4) At the positioning step, the sterilization target 10 is stopped at the position in which an average dose to the bottom region of the dented portion 12 is 0.1 mJ/cm$^2$ or more, and preferably 5 mJ/cm$^2$ or more when ultraviolet light is applied for one second from the LED elements 22 included in the plurality of light sources 22 provided in each irradiation unit.

As a result, an amount of ultraviolet light required for sterilization can be applied to the bottom region of the dented portion 12 in a short time.

(5) At the ultraviolet light irradiation step, ultraviolet light is applied to the different positions on the sterilization target 10 from the LED element 22 included in at least one of the plurality of light sources 20 and the LED element 22 included in the other one included in the plurality of light sources 20.

As a result, ultraviolet light can be efficiently applied to the dented portion 12, thus enabling improvement in sterilization efficiency.

(6) As the ultraviolet light, ultraviolet C wave is applied.

As a result, sterilization power can be improved as compared with when the ultraviolet light is ultraviolet A wave or ultraviolet B wave.

(7) The sterilization target 10 is a cap configured to close the opening portion of a container for accommodating an article.

As a result, in many caps having the uneven shape 16 due to adhesion to a container and easy opening and closing thereof, ultraviolet light can be efficiently applied to the shaded region SE formed by the protruded portion 14 in the sterilization target 10, thereby enabling improvement in sterilization efficiency.

Particularly, in caps requiring cleanness to accommodate food and drinks, such as caps of containers for accommodating drinks, sterilization efficiency can be improved.

(8) The cap exemplified as the sterilization target 10 includes the cylindrical portion 10a having one end closed at the bottom face portion 10b and the other end open. In addition to this, the protruded portion 14 is the annular protrusion formed at the position spaced by a gap from the inner diameter surface of the cylindrical portion 10a on the bottom face portion 10b, and the dented portion 12 is the annular groove formed between the inner diameter surface of the cylindrical portion 10a and the protruded portion 14 on the bottom face portion 10b.

As a result, the sterilization target 10 having the circular uneven shape 16 can be effectively sterilized.

(9) The plurality of light sources 20 are arranged to be equidistantly spaced apart from each other along the circle facing the annular dented portion 12, and ultraviolet light is applied to the dented portion 12 from the plurality of light sources 20.

As a result, variation in the ultraviolet light dose to the annular dented portion 12 can be suppressed, thus enabling effective sterilization of the sterilization target 10 having the circular uneven shape 16.

In addition, the sterilization device 1 of the first embodiment can provide the following effects.

(10) The sterilization device 1 includes the plurality of light sources 20 configured to apply ultraviolet light, in which each of the plurality of light sources 20 includes the LED element configured to apply ultraviolet light. In addition to this, in the state where the sterilization target 10 arranged at the previously set irradiation position face the plurality of light sources 20, ultraviolet light is simultaneously applied from each of the plurality of LED elements, and reaches the sterilization target 10.

Thus, ultraviolet light can be efficiently applied to the shaded region SE formed by the protruded portion 14 in the sterilization target 10, thereby enabling improvement in sterilization efficiency.

As a result, there can be provided the sterilization device 1 capable of effectively sterilizing the sterilization target 10 having the uneven shape 16.

In addition to this, since the time required for sterilization can be shortened, power consumption can be reduced, as well as the lifetime of the LED elements can be extended. Additionally, heat generated from the LED elements can be reduced.

(11) At least one of the LED elements 22 included in the plurality of light sources 20 is arranged to apply ultraviolet light by directing the direction of a light beam with maximum light intensity toward the dented portion 12.

As a result, ultraviolet light can be efficiently applied to the dented portion 12, thus enabling improvement in sterilization efficiency.

Modifications (1) In the first embodiment, as illustrated in FIG. 2 and the like, the directions of light emitted from the LED elements included in the light sources 20 are directed toward the dented portion 12. However, the invention is not limited thereto.

Figure 7:
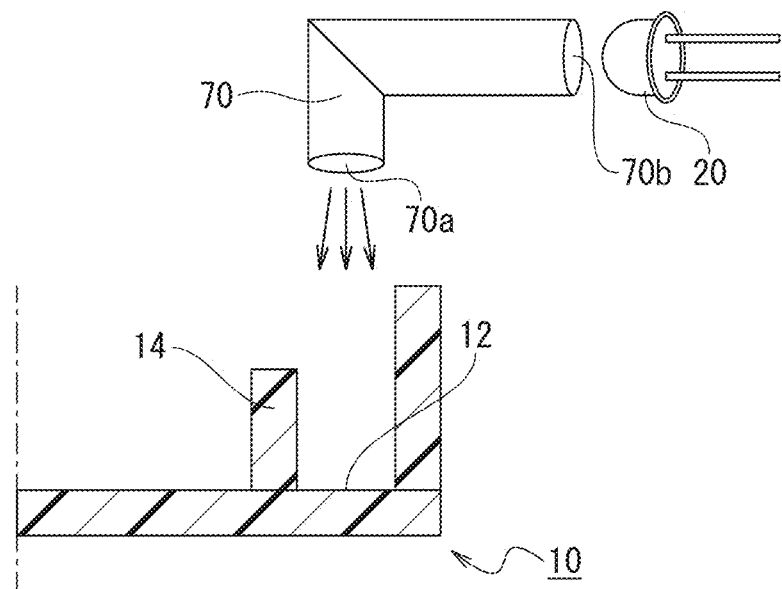
FIG. 7 is a diagram illustrating the schematic structure of a sterilization device according to a modification of the first embodiment of the present invention.

Specifically, for example, as illustrated in FIG. 7, the directions of light emitted from the LED elements included in the light source 20 may be directed toward a direction along the bottom face of the dented portion 12, and additionally, ultraviolet light may be applied to the dented portion 12 via a light guide tube 70 configured to transmit and guide ultraviolet light.

The light guide tube 70 is formed using, for example, optical fiber or the like, and arranged in such a manner as to direct one end 70a of the light guide tube 70 toward the dented portion 12. Furthermore, the light source 20 is arranged at a position in which the directions of light emitted from the LED elements are directed toward an other end 70b of the light guide tube 70.

This structure can improve flexibility in arrangement of the light source 20.

(2) In the first embodiment, as illustrated in FIG. 2 and the like, the main emission direction MRa of the light source 20a is directed toward the first irradiation position 12a, and the main emission direction MRb of the light source 20b is directed toward the second irradiation position 12b. However, the invention is not limited thereto.

Figure 8:
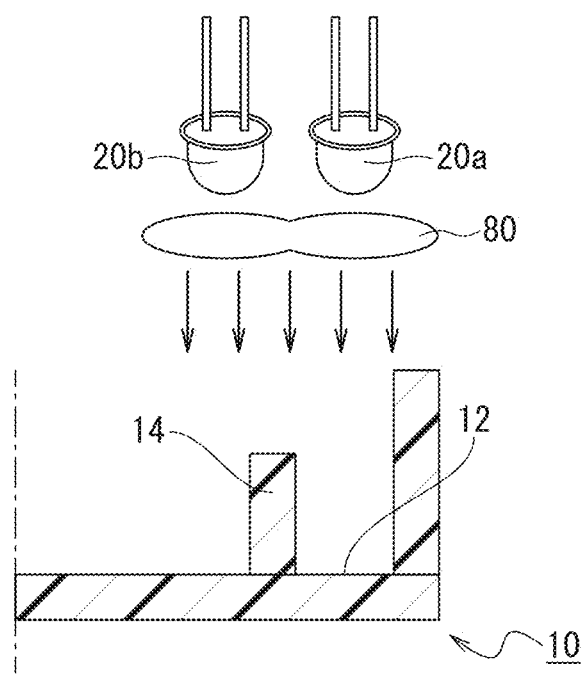
FIG. 8 is a diagram illustrating the schematic structure of a sterilization device according to a modification of the first embodiment of the present invention.

Specifically, for example, as illustrated in FIG. 8, the directions of light emitted from the LED elements included in the light sources 20a and 20b aligned in parallel are directed toward the dented portion 12. Furthermore, an optical member 80 may be arranged between the light sources 20a and 20b and the sterilization target 10 to convert light emitted from the LED elements included in the light sources 20a and 20b to parallel light.

The optical member 80 is formed using, for example, a lens or the like. Then, the optical member 80 is arranged at a position in which light emitted from the LED elements include in the light sources 20a and 20b is converted to parallel light by the optical member 80 and applied to the bottom region of the dented portion 12.

This structure can improve positional deviation allowance in arrangement of the plurality of light sources 20.

Second Embodiment

Hereinafter, a second embodiment of the present invention will be described with reference to the drawings.
(Structure)

With reference to FIG. 1 and FIG. 2 and using FIG. 9 to FIG. 11, the structure of the second embodiment will be described.

The structure of the second embodiment is the same as that of the first embodiment described above except for the structures of the light sources 20 and the irradiation controller 50.

The other structures are the same as those of the first embodiment described above, and thus description thereof will be omitted.
(Light Source)

Each light source 20 applies ultraviolet light.

In the second embodiment, as one example, a case where the sterilization device 1 includes four light sources 20a to 20d will be described. Note that in the drawings and the description hereinbelow, the light source 20 arranged upstream of the direction in which a sterilization target 10 is transferred (indicated as "TRANSFER DIRECTION" in FIG. 9 and FIG. 10) is defined as light source 20a, and the light source 20 arranged downstream of the transfer direction is defined as light source 20b.

Similarly, the light source 20 arranged between the light source 20a and the light source 20b, and arranged above the light sources 20a and 20b in a vertical direction (indicated as "VERTICAL DIRECTION" in FIG. 9 and FIG. 11) is defined as light source 20c. Additionally, the light source 20 arranged between the light source 20a and the light source 20b, and arranged below the light sources 20a and 20b is defined as light source 20d.

Figure 10:
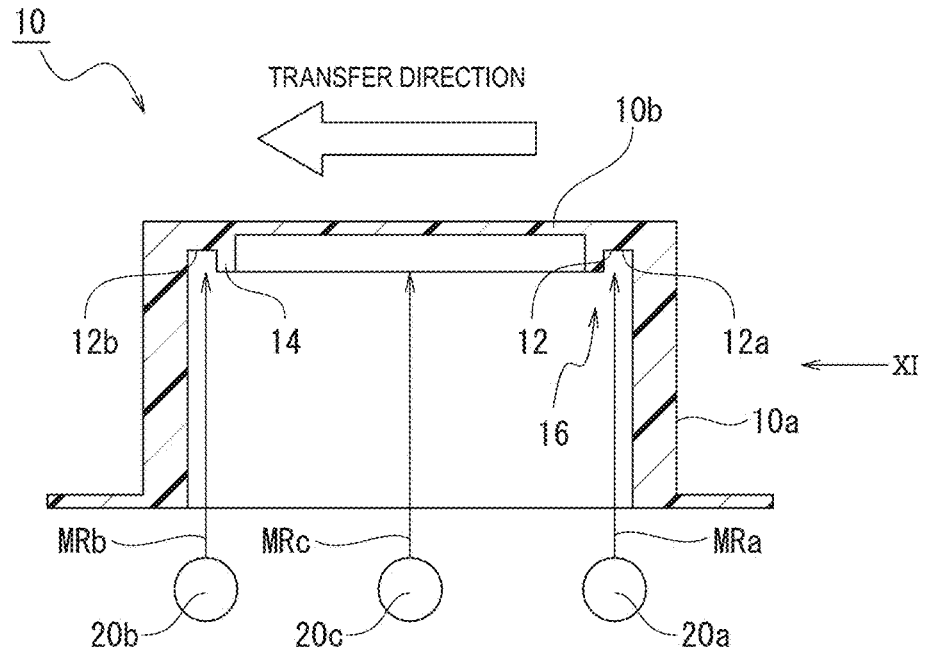
FIG. 10 is a plan view illustrating the schematic structure of the sterilization device according to the second embodiment of the present invention.

Note that FIG. 10 illustrates a cross-sectional diagram of the sterilization target 10 taken along the center line in the transfer direction. Additionally, FIG. 11 illustrates a cross-sectional diagram of the sterilization target 10 taken along the center line in the vertical direction.

Each light source 20 applies ultraviolet light.

The main emission direction MRa, the main emission direction MRb, a main emission direction MRc of the LED element included in the light source 20c, and a main emission direction MRd of the LED element included in the light source 20d are directed toward different positions on the sterilization target 10 arranged at an irradiation position.

Figure 9:
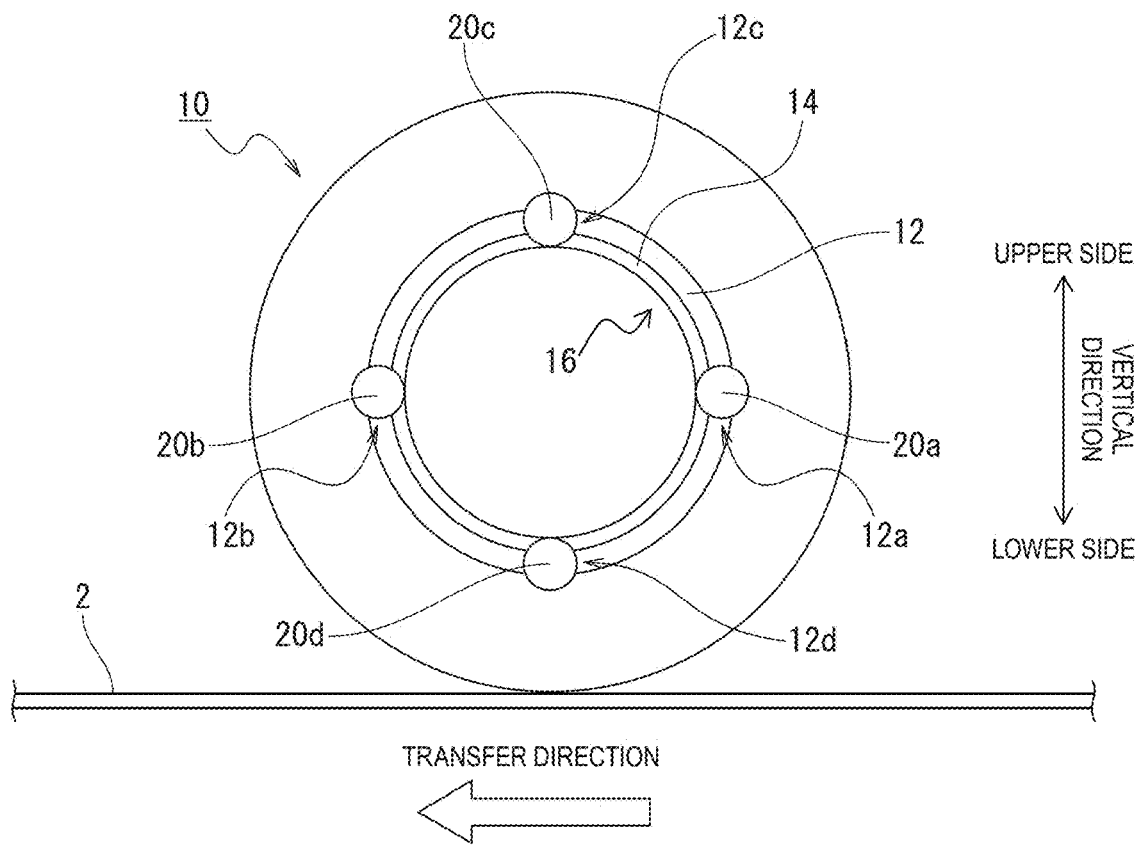
FIG. 9 is a diagram illustrating the schematic structure of a sterilization device according to a second embodiment of the present invention.

Specifically, as illustrated in FIG. 9 and FIG. 10, the main emission direction MRa is directed toward the first irradiation position 12a positioned on an upstream side of the transfer direction in the dented portion 12 forming the uneven shape 16. In addition to this, as illustrated in FIG. 9 and FIG. 10, the main emission direction MRb is directed toward the second irradiation position 12b positioned on a downstream side of the transfer direction in the dented portion 12 forming the uneven shape 16.

Figure 11:
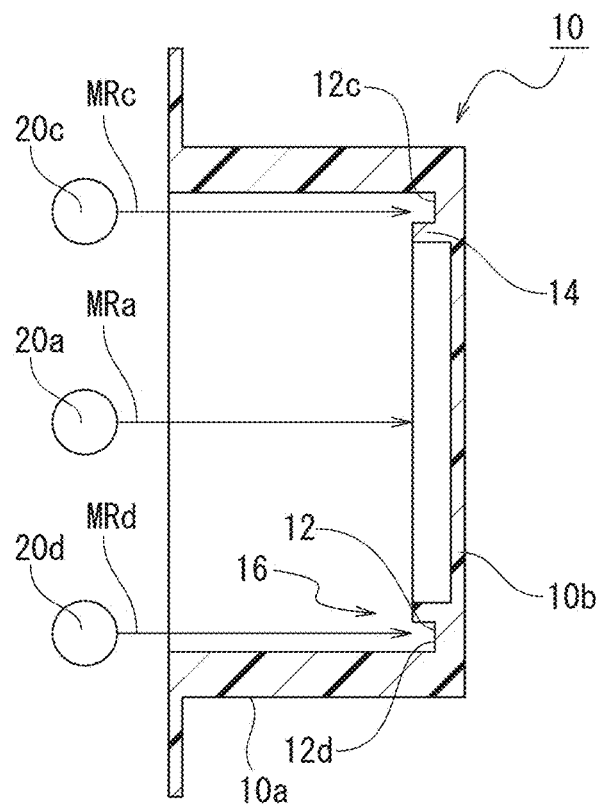
FIG. 11 is a diagram as seen from an arrow line XI in FIG. 10.

Furthermore, as illustrated in FIG. 9 and FIG. 11, the main emission direction MRc is directed toward a third irradiation position 12c, which is a portion positioned between and above the first irradiation position 12a and the second irradiation position 12b in the dented portion 12 forming the uneven shape 16. In addition to this, as illustrated in FIG. 9 and FIG. 11, the main emission direction MRd is directed toward a fourth irradiation position 12d, which is a portion positioned between and below the first irradiation position 12a and the second irradiation position 12b in the dented portion 12 forming the uneven shape 16.

Note that, similarly to the first embodiment described above, the sterilization target 10 is a cylindrical cap, and thus, the first irradiation position 12a, the second irradiation position 12b, the third irradiation position 12c, and the fourth irradiation position 12d indicate different positions on the dented portion 12 having the same structure. Additionally, the first irradiation position 12a, the second irradiation position 12b, the third irradiation position 12c, and the fourth irradiation position 12d are equidistantly arranged on the dented portion 12 formed into the cylindrical shape.

Additionally, the plurality of light sources 20a to 20d are arranged to be equidistantly spaced apart from each other along a circle (along a virtual circle) facing the annular dented portion 12.

In other words, the first irradiation position 12a, the second irradiation position 12b, the third irradiation position 12c, and the fourth irradiation position 12d are arranged at an equal interval (a 90 degree interval) in a circumferential direction of the dented portion 12 in the dented portion 12 formed into the cylindrical shape.

Accordingly, the first irradiation position 12a, the second irradiation position 12b, the third irradiation position 12c, and the fourth irradiation position 12d are arranged at positions in different ones of quadrants divided with reference to the center of the surface facing each light source 20 in the sterilization target 10 (the center of the bottom face portion 10b).

(Irradiation Controller)

When the irradiation controller 50 receives a transfer stop signal input from the position controller 40 after receiving a target detection signal input from the proximity sensor 30, it allows the light sources 20a and 20b to apply ultraviolet C wave. Then, after stopping irradiation with ultraviolet C wave from the light sources 20a and 20b, the irradiation controller 50 allows the light sources 20c and 20d to apply ultraviolet C wave.

Accordingly, at least one (the light sources 20a, 20b) of the plurality of light sources 20 and the other one (the light sources 20c, 20d) of the plurality of light sources 20 apply ultraviolet light at mutually different timings.

In addition, positions toward which the main emission directions MR of the LED elements included in the light sources 20 configured to apply ultraviolet light at mutually different timings are directed are equidistantly arranged on the surface of the sterilization target 10 to which ultraviolet light is applied.

(Sterilization Method)

With reference to FIG. 1, FIG. 2, and FIG. 9 to FIG. 11, a description will be given of a sterilization method for sterilizing the sterilization target 10, which is performed using the sterilization device 1 of the second embodiment.

The sterilization method includes a transfer step, a positioning step, and an ultraviolet light irradiation step. Note that the transfer step and the positioning step are the same as those of the first embodiment described above, and thus, description thereof will be omitted.

(Ultraviolet Light Irradiation Step)

The ultraviolet light irradiation step is a step of applying ultraviolet light to the sterilization target 10 from the plurality of light sources 20.

Additionally, the ultraviolet light irradiation step in the second embodiment includes an ultraviolet light irradiation pre-stage step and an ultraviolet light irradiation post-stage step, which is a post-step after the ultraviolet light irradiation pre-stage step.

At the ultraviolet light irradiation pre-stage step, the main emission direction MRa is directed toward the first irradiation position 12a, and the main emission direction MRb is directed toward the second irradiation position 12b. Then, in this state, ultraviolet light is applied from the LED element included in the light source 20a and the LED element included in the light source 20b.

At the ultraviolet light irradiation post-stage step, first, irradiation with ultraviolet light from the light sources 20 (the light sources 20a and 20b) applying the ultraviolet light at the ultraviolet light irradiation pret-stage step is stopped.

After that, ultraviolet light is applied from the LED element included in the light source 20c and the LED element included in the light source 20d in a state where the main emission direction MRc is directed toward the third irradiation position 12c, and the main emission direction MRd is directed toward the fourth irradiation position 12d. In other words, at the ultraviolet light irradiation step in the second embodiment, ultraviolet light is applied at the mutually different timings to positions in different ones of quadrants divided with reference to the center of the surface facing the light sources 20 in the sterilization target 10.

(Operation and Effects)

With reference to FIG. 1 to FIG. 11, a description will be given of operation and effects of the second embodiment. Note that description of the same operation and effects as those of the first embodiment described above may be omitted.

When sterilizing the sterilization target 10 using the sterilization device 1, first, the sterilization target 10 transferred by being placed on the moving unit 2 is arranged at an irradiation position, and then, is irradiated with ultraviolet light from the light sources 20a and 20b.

After that, after stopping the irradiation with ultraviolet light from the light sources 20a and 20b, ultraviolet light is applied from the light sources 20c and 20d.

As described above, on the bottom face of the sterilization target 10 are formed the dented portion 12 and the protruded portion 14. Thus, with the configuration of the sterilization device including the conventional structure, there arise problems where sterilization is insufficient and sterilization takes time (see FIG. 4 and FIG. 5).

By contrast, with the sterilization device 1 of the second embodiment, each of the main emission directions MRa to MRd is directed toward different positions on the sterilization target 10.

Thus, the sterilization device 1 of the second embodiment enables ultraviolet light to be efficiently applied to the shaded region SE formed by the protruded portion 14, so that sterilization efficiency can be improved as compared with the sterilization device including the conventional structure. Additionally, the time required for sterilization can be shortened.

Furthermore, with the sterilization device 1 of the second embodiment, after irradiating with ultraviolet light from the light sources 20a and 20b and then stopping irradiating with ultraviolet light therefrom, ultraviolet light is applied from the light sources 20c and 20d. In other words, the sterilization device 1 of the second embodiment allows at least one of the plurality of light sources 20 and the other one of the plurality of light sources 20 to apply ultraviolet light at mutually different timings, whereby ultraviolet light irradiation is performed in multiple stages (two stages).

Thus, as compared with when ultraviolet light is applied simultaneously from all the light sources 20a to 20d, the number of the light sources 20 for simultaneously applying ultraviolet light can be reduced.

Furthermore, ultraviolet light can be applied in multiple stages to a region where light beams emitted from each of the light sources 20 toward directions other than the main emission directions MR overlap with each other, so that the time of ultraviolet light irradiation can be increased without increasing the amount of energy consumption. In addition to this, the structure of the heat dissipation device included in each of the light sources 20 can be simplified. Additionally, in the sterilization device 1 of the second embodiment, the positions toward which the main emission directions MR of the LED elements included in the light sources 20 configured to apply ultraviolet light at mutually different timings are directed are equidistantly arranged on the surface of the sterilization target 10 to which ultraviolet light is applied.

Thus, ultraviolet light can be efficiently applied in multiple stages to the region where light beams emitted in directions other than the main emission direction MR from each light source 20 overlap with each other.

Note that the above-described second embodiment is one example of the present invention, and the invention is not limited thereto. Even with embodiments other than the embodiment, various modifications can be made according to design and the like without departing from the scope of the technological ideas of the present invention.

Effects of Second Embodiment

The sterilization method of the second embodiment can provide the following effects:

(1) Ultraviolet light is applied at mutually different timings from at least one (the light sources 20a, 20b) of the plurality of light sources 20 and the other one (the light sources 20c, 20d) of the plurality of light sources 20.

Thus, as compared with when ultraviolet light is applied simultaneously from all the light sources 20, the number of the light sources 20 for simultaneously applying ultraviolet light can be reduced.

As a result, output of the light sources 20 can be reduced, thus enabling reduction in the amount of energy consumption.

Additionally, since ultraviolet light can be applied in multiple stages to the region where light beams emitted in directions other than the main emission direction MR from each light source 20 overlap with each other, the time of ultraviolet light irradiation can be increased without increasing the amount of energy consumption. Furthermore, the structure of the heat dissipation device included in each of the light sources 20 can be simplified.

(2) Ultraviolet light is applied at mutually different timings to positions in different ones of quadrants divided with reference to the center of the surface facing the light sources 20 in the sterilization target 10.

As a result, ultraviolet light can be efficiently applied in multiple stages to the region where light beams emitted in directions other than the main emission direction MR from each light source 20 overlap with each other.

Modifications (1) In the second embodiment, the first irradiation position 12a, the second irradiation position 12b, the third irradiation position 12c, and the fourth irradiation position 12d are positioned in different ones of the quadrants divided with reference to the center of the surface facing each light source 20 in the sterilization target 10. However, the present invention is not limited thereto.

In other words, the first irradiation position 12a, the second irradiation position 12b, the third irradiation position 12c, and the fourth irradiation position 12d may be positioned in the same one(s) of the quadrants divided with reference to the center of the surface facing each light source 20 in the sterilization target 10.

Third Embodiment

Hereinafter, a third embodiment of the present invention will be described with reference to the drawings.
(Structure)

With reference to FIG. 1 to FIG. 11 and using FIG. 12 and FIGS. 13A to 13C, the structure of the third embodiment will be described.

Figure 12:
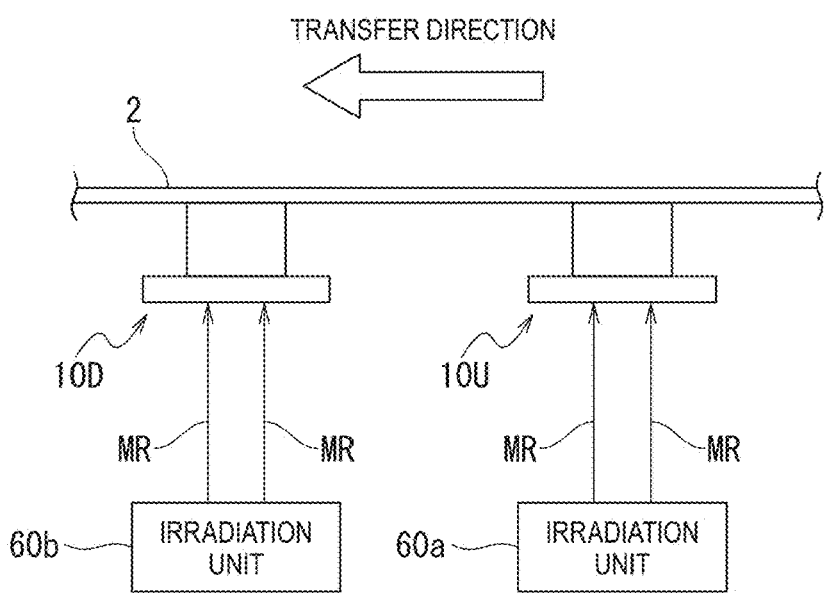
FIG. 12 is a diagram illustrating the schematic structure of a sterilization device according to a third embodiment of the present invention.

A sterilization device 1 illustrated in FIG. 12 is a device configured to apply ultraviolet light from a plurality of irradiation units 60 to a plurality of sterilization targets 10 transferred by being placed on a moving unit 2 included in a transfer device. Note that FIG. 12 illustrates a positional relationship between the moving unit 2 and the sterilization targets 10, as a schematic relationship.

In addition, the sterilization device 1 includes the plurality of irradiation units 60.

Note that in the third embodiment, as one example, a case where the sterilization device 1 includes two irradiation units 60a and 60b will be described. Accordingly, in the third embodiment, a case where the two irradiation units 60a and 60b apply ultraviolet light to two sterilization targets 10U and 10D transferred by being placed on the moving unit 2 will be described.

Additionally, in FIG. 12 and the description hereinbelow, the sterilization target 10 arranged at an upstream of the transfer direction is defined as the sterilization target 10U, and the sterilization target 10 arranged at a downstream of the transfer direction is defined as the sterilization target 10D. Similarly, the irradiation unit 60 arranged at the upstream of the transfer direction is defined as the irradiation unit 60a, and the irradiation unit 60 arranged at the downstream of the transfer direction is defined as the irradiation unit 60b.

The irradiation units 60a and 60b are aligned at the same interval as the interval between the sterilization targets 10U and 10D adjacent to each other in the transfer direction of the sterilization target 10.

Each irradiation unit 60 includes light sources 20, a proximity sensor 30, a position controller 40, and an irradiation controller 50. Note that the structures of the proximity sensor 30 and the position controller 40 included in each irradiation unit 60 are the same as those of the first embodiment described above, and thus, description thereof will be omitted.

(Light Source)

Each light source 20 applies ultraviolet light.

Figure 13A:
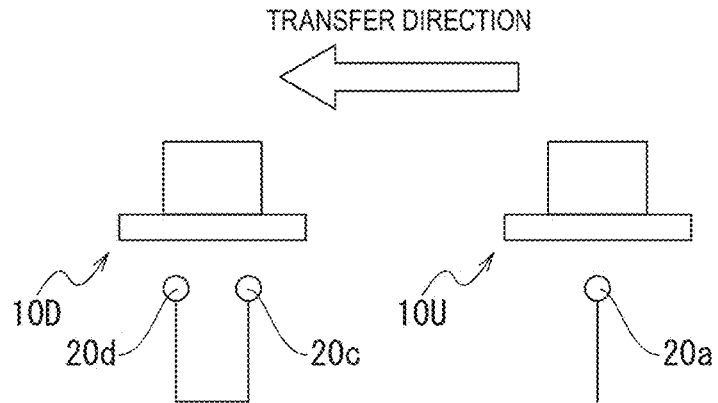
FIGS. 13A to 13C are diagrams illustrating the schematic structure of the sterilization device according to the third embodiment of the present invention.
Figure 13B:
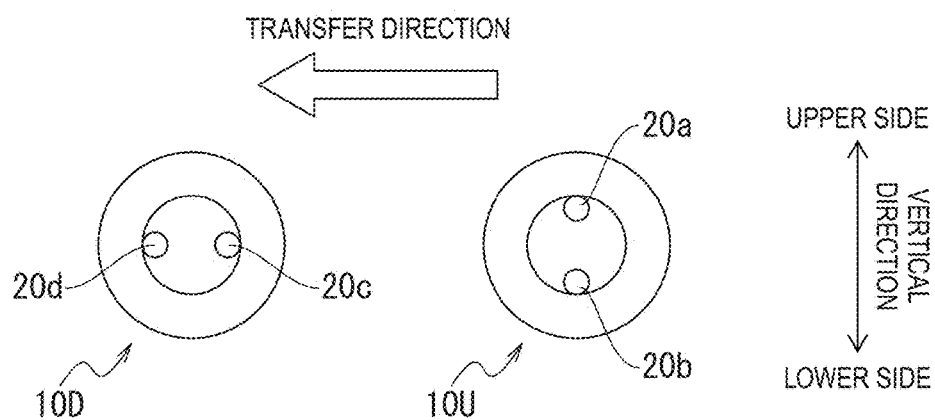
Figure 13C:
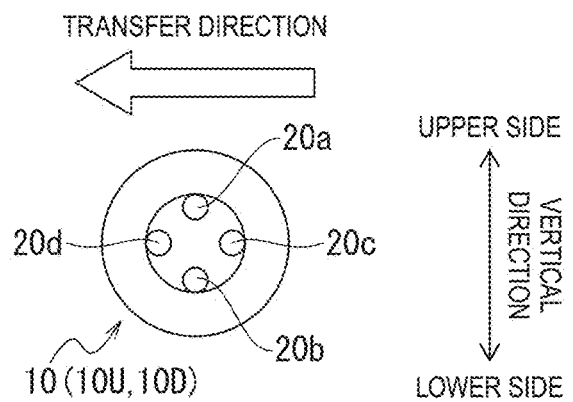

In the third embodiment, as one example, a case where the irradiation unit 60a includes two light sources 20a and 20b, and the irradiation unit 60b includes two light sources 20c and 20d will be described, as illustrated in FIGS. 13A to 13C.

The light source 20a is a light source 20 arranged above the center of the sterilization target 10.

The light source 20b is a light source 20 arranged below the center of the sterilization target 10.

In addition, the light sources 20a and 20b are arranged at an equal interval (a 180 degree interval) on a circle (on a virtual circle) facing the annular dented portion 12.

The main emission direction of an LED element included in the light source 20a and the main emission direction of an LED element included in the light source 20b are directed toward different positions on the sterilization target 10U (see FIG. 9 and FIG. 10).

The light source 20c is a light source 20 arranged at an upstream of a direction in which the sterilization target 10 is transferred (indicated as "TRANSFER DIRECTION" in FIG. 12 and FIGS. 13A to 13C).

The light source 20d is a light source 20 arranged at a downstream of the transfer direction.

In addition, the light sources 20c and 20d are arranged at an equal interval (a 180 degree interval) on the circle (on the virtual circle) facing the annular dented portion 12.

The main emission direction of the LED element included in the light source 20c and the main emission direction of the LED element included in the light source 20d are directed toward different positions on the sterilization target 10D (see FIG. 9 and FIG. 10).

Accordingly, the light sources 20a and 20b included in the irradiation unit 60a and the light sources 20c and 20d included in the irradiation unit 60b are arranged to be complementary to each other, as illustrated in FIG. 13C. By doing this, as illustrated in FIG. 13C, the light sources 20a to 20d are arranged to be equidistantly spaced apart from each other along the circle facing the annular dented portion 12.

In other words, the sterilization device 1 of the third embodiment is formed by aligning the plurality of irradiation units 60 each including the plurality of light sources 20 in the transfer direction of the sterilization target 10. In addition to this, the LED elements included in the light sources 20 provided in the respective plurality of irradiation units 60 are respectively arranged on the circumferences of circles, the distances between the outer diameters of the respective circles and the centers of the surfaces facing the light sources 20 in the respective sterilization targets 10 being equal to the other.

(Irradiation Controller)

When the irradiation controller 50 receives a transfer stop signal input from the position controller 40 after receiving a target detection signal input from the proximity sensor 30, it allows the light sources 20a and 20b to apply ultraviolet C wave to the sterilization target 10U. In addition to this, the irradiation controller 50 allows the light sources 20c and 20d to apply ultraviolet C wave to the sterilization target 10D.

Accordingly, in the third embodiment, the plurality of irradiation units 60 each including the plurality of light sources 20 are arranged at the same interval as the interval between the sterilization targets 10U and 10D adjacent to each other in the transfer direction of the sterilization target 10. In addition to this, when the sterilization targets 10U and 10D move to previously set irradiation positions, the plurality of light sources 20 provided in the irradiation units 60a and 60b simultaneously apply ultraviolet light to the sterilization targets 10U and 10D at the irradiation positions.

(Sterilization Method)

With reference to FIG. 1 to FIG. 12, and FIGS. 13A to 13C, a description will be given of a sterilization method for sterilizing the sterilization targets 10, which is performed using the sterilization device 1 of the third embodiment.

The sterilization method includes a transfer step, a positioning step, and an ultraviolet light irradiation step. Note that since the transfer step is the same as that of the first embodiment described above, description thereof will be omitted.

(Positioning Step)

The positioning step is a step of arranging the sterilization targets 10U and 10D transferred by being placed on the moving unit 2 at irradiation positions.

Thus, at the positioning step, the sterilization target 10U is arranged at a position in which the main emission direction of the LED element included in the light source 20a and the main emission direction of the LED element included in the light source 20b are directed toward different positions on the sterilization target 10U. In addition to this, at the positioning step, the sterilization target 10D is arranged at a position in which the main emission direction of the LED element included in the light source 20c and the main emission direction of the LED element included in the light source 20d are directed toward different positions on the sterilization target 10D.

Note that, at the positioning step that is initially performed for the plurality of sterilization targets 10, only the sterilization target 10U transferred by being placed on the moving unit 2 is arranged at an irradiation position (an ultraviolet light irradiation step).

The ultraviolet light irradiation step is a step of applying ultraviolet light to the sterilization targets 10 from the plurality of light sources 20.

At the ultraviolet light irradiation step, first, the main emission direction MRa is directed toward the first irradiation position 12a of the sterilization target 10U, and the main emission direction MRb is directed toward the second irradiation position 12b of the sterilization target 10U. In addition to this, at the ultraviolet light irradiation step, the main emission direction MRc is directed toward the third irradiation position 12c of the sterilization target 10D, and the main emission direction MRd is directed toward the fourth irradiation position 12d of the sterilization target 10D. Then, ultraviolet light is applied from the LED element included in the light source 20a, the LED element included in the light source 20b, the LED element included in the light source 20c, and the LED element included in the light source 20d.

In other words, at the ultraviolet light irradiation step of the third embodiment, when the sterilization targets 10U and 10D move to the previously set irradiation positions, ultraviolet light is simultaneously applied to the sterilization targets 10U and 10D at the irradiation positions from the plurality of light sources 20a to 20d provided in the two irradiation units 60a and 60b.

Note that, at the ultraviolet light irradiation step that is initially performed for the plurality of sterilization targets 10, when only the sterilization target 10U moves to the irradiation position, ultraviolet light is applied to the sterilization target 10U at the irradiation position from the plurality of light sources 20a and 20b provided in the irradiation unit 60a.

(Operation and Effects)

With reference to FIG. 1 to FIG. 12, and to FIGS. 13A to 13C, operation and effects of the third embodiment will be described. Note that description of the same operation and effects as those of the first embodiment described above may be omitted.

When sterilizing the sterilization targets 10 using the sterilization device 1, first, the sterilization targets 10U and 10D transferred by being placed on the moving unit 2 are arranged at the irradiation positions, and then, are simultaneously irradiated with ultraviolet light from the light sources 20a and 20b and the light sources 20c and 20d.

Thus, in the sterilization device 1 of the third embodiment, ultraviolet light is simultaneously applied from the light sources 20a to 20d. In other words, in the sterilization device 1 of the third embodiment, at least one of the plurality of light sources 20 and the other one of the plurality of light sources 20 simultaneously apply ultraviolet light at mutually different positions, thereby performing ultraviolet light irradiation in multiple stages (two stages).

Therefore, as compared with when a single irradiation unit includes four light sources 20, from which ultraviolet light is simultaneously applied to a single sterilization target 10, the number of the light sources 20 for applying ultraviolet light to the single sterilization target 10 can be reduced.

Furthermore, ultraviolet light can be applied in multiple stages to a region where light beams emitted in directions other than the main emission directions MR from each of the light sources 20 overlap with each other, so that the time of ultraviolet light irradiation can be increased without increasing the amount of energy consumption. In addition to this, the structure of the heat dissipation device included in each of the light sources 20 can be simplified.

Additionally, in the sterilization device 1 of the third embodiment, the positions toward which the main emission directions MR of the LED elements included in the light sources 20 configured to apply ultraviolet light at mutually different timings are directed are equidistantly arranged on the surfaces of the sterilization targets 10 to which ultraviolet light is applied.

By doing this, ultraviolet light can be efficiently applied in multiple stages to the region where light beams emitted in directions other than the main emission direction MR from each light source 20 overlap with each other.

Note that the above-described third embodiment is one example of the present invention, and the invention is not limited thereto. Even with embodiments other than the embodiment, various modifications can be made according to design and the like without departing from the scope of the technological ideas of the present invention.

Effects of Third Embodiment

The sterilization method of the third embodiment can provide the following effects:

(1) The plurality of irradiation units 60 each including the plurality of light sources 20 are aligned in the transfer direction of the sterilization targets 10. In addition to this, the LED elements included in the light sources 20 provided in the respective plurality of irradiation units 60 are respectively arranged on the circumferences of the circles, the distances between the outer diameters of the respective circles and the centers of the surfaces facing the light sources 20 in the respective sterilization targets 10 being equal.

Thus, as compared with when ultraviolet light is simultaneously applied to a single sterilization target 10 from all the light sources 20 provided in a single irradiation unit, the number of the light sources 20 for applying ultraviolet light to the single sterilization target 10 can be reduced.

As a result, output of the light sources 20 can be reduced, thus enabling reduction in the amount of energy consumption.

Additionally, since ultraviolet light can be applied in multiple stages to the region where light beams emitted in directions other than the main emission direction MR from each light source 20 overlap with each other, the time of ultraviolet light irradiation can be increased without increasing the amount of energy consumption. Furthermore, the structure of the heat dissipation device included in each of the light sources 20 can be simplified.

(2) The plurality of irradiation units 60 each including the plurality of light sources 20 is aligned at the same interval as the interval between the sterilization targets 10U and 10D adjacent to each other in the transfer direction of the sterilization targets 10. In addition to this, when the sterilization targets 10U and 10D move to the previously set irradiation positions, ultraviolet light is simultaneously applied to the sterilization targets 10U and 10D at the irradiation positions from the plurality of light sources 20 included in the irradiation units 60a and 60b.

Thus, as compared with when ultraviolet light is simultaneously applied to the single sterilization target 10 from all the light sources 20 provided in the single irradiation unit, the number of the light sources 20 for applying ultraviolet light to the single sterilization target 10 can be reduced.

As a result, output of the light sources 20 can be reduced, thus enabling reduction in the amount of energy consumption.

Modifications (1) In the third embodiment, the irradiation unit 60a includes the two light sources 20a and 20b, and the irradiation unit 60b includes the two light sources 20c and 20d. However, the present invention is not limited thereto.

Figure 14A:
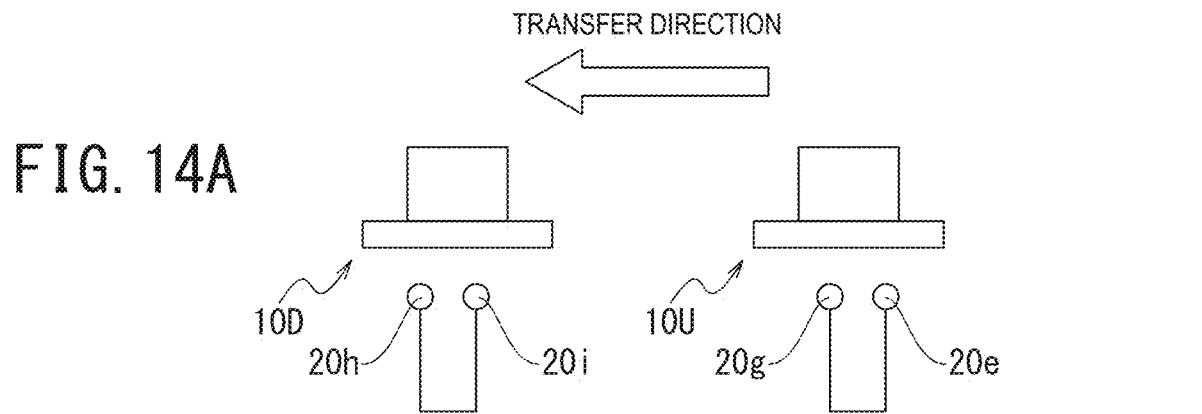
FIGS. 14A to 14C are diagrams illustrating the schematic structure of a sterilization device according to a modification of the third embodiment of the present invention.
Figure 14B:
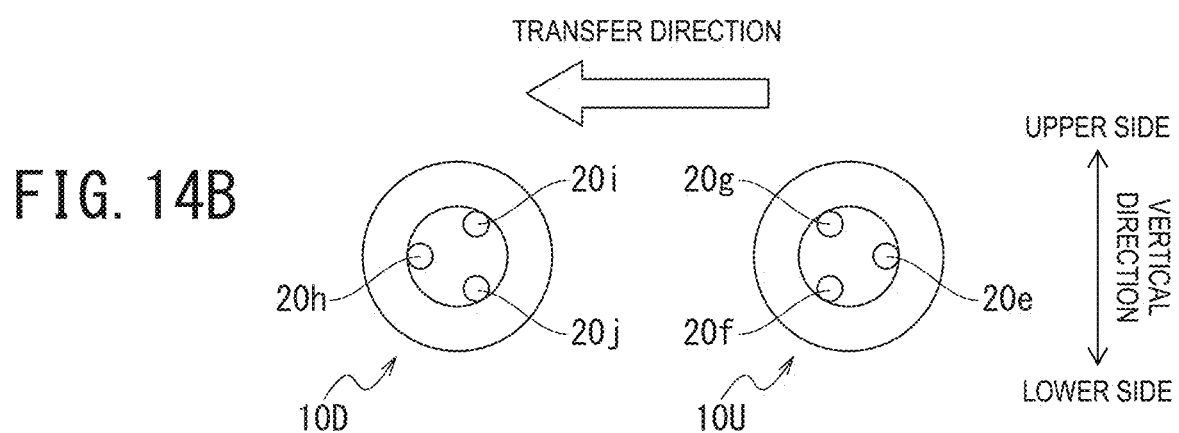
Figure 14C:
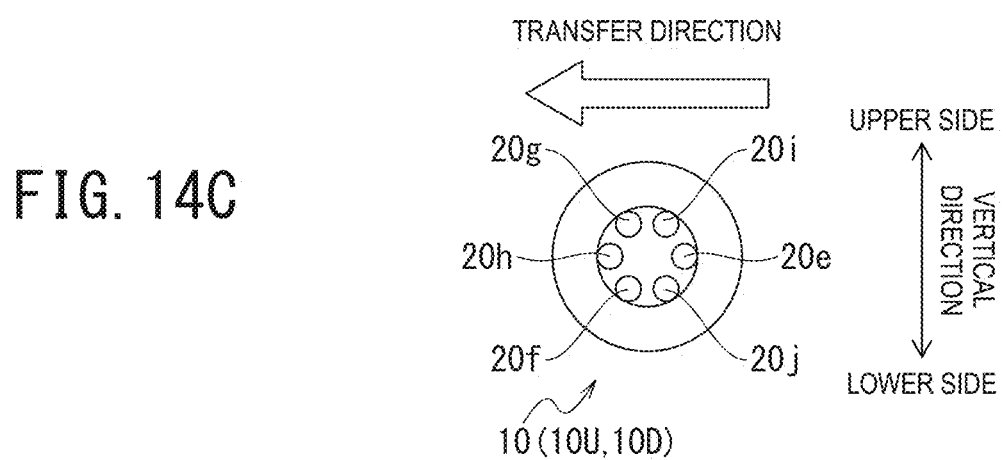

Specifically, for example, as illustrated in FIGS. 14A to 14C, the irradiation unit 60a may include three light sources 20e to 20g, and the irradiation unit 60b may include three light sources 20h to 20j.

In this case, the three light sources 20e to 20g are respectively arranged at each apex angle of an equilateral triangle as seen from the bottom face of the sterilization target 10. Additionally, the three light sources 20h to 20j are respectively arranged at each apex angle of an equilateral triangle as seen from the bottom face of the sterilization target 10, and respective main emission directions thereof are arranged in such a manner as to be directed toward positions between the main emission directions of the light sources 20e to 20g.

In other words, the light sources 20e to 20g are arranged at an equal interval (a 120 degree interval) along a circle (along a virtual circle) facing the annular dented portion 12. Similarly, the light sources 20h to 20j are arranged at an equal interval (a 120 degree interval) on a circle (on a virtual circle) facing the annular dented portion 12.

Additionally, one (the light source 20e) of the three light sources 20e to 20g and one (the light source 20h) of the three light sources 20h to 20j are arranged in parallel in the transfer direction.

Accordingly, the three light sources 20e to 20g of the irradiation unit 60a and the three light sources 20h to 20j of the irradiation unit 60b are arranged to be complementary to each other, as illustrated in FIG. 14C. By doing this, the light sources 20e to 20j are arranged to be equidistantly spaced apart from each other along the circle facing the annular dented portion 12, as illustrated in FIG. 14C.

Then, when the irradiation controller 50 receives a transfer stop signal input from the position controller 40 after receiving a target detection signal input from the proximity sensor 30, it allows the light sources 20e to 20g to apply ultraviolet C wave to the sterilization target 10U. In addition to this, the irradiation controller 50 allows the light sources 20h to 20j to apply ultraviolet C wave to the sterilization target 10D.

EXAMPLES

Sterilization devices of Examples 1 to 5 and a sterilization device of Comparative Example will be described with reference to the first through third embodiments and using the following Examples.

Example 1

The sterilization device of Example 1 includes the same structure as that of the first embodiment. In other words, the sterilization device of Example 1 includes the structure in which two light sources are included, and the main emission directions of LED elements of each light source are directed toward two irradiation positions equidistantly arranged in a dented portion formed into an annular shape (see FIG. 1 and FIG. 2)

Furthermore, the sterilization device of Example 1 includes a structure configured to simultaneously apply ultraviolet light from the two light sources.

Example 2

The sterilization device of Example 2 includes a structure in which four light sources are included, and the main emission directions of LED elements of each light source are directed toward four irradiation positions equidistantly arranged in a dented portion formed into an annular shape (see FIG. 9 to FIG. 11)

Example 3

The sterilization device of Example 3 includes a structure in which six light sources are included, and the main emission directions of LED elements of each light source are directed toward six irradiation positions equidistantly arranged in a dented portion formed into an annular shape.

Example 4

The sterilization device of Example 4 includes a structure in which eight light sources are included, and the main emission directions of LED elements of each light source are directed toward eight irradiation positions equidistantly arranged in a dented portion formed into an annular shape.

Example 5

The sterilization device of Example 5 includes a structure in which five light sources are included, and the main emission directions of LED elements of four of the five light sources are directed toward four irradiation positions equidistantly arranged in a dented portion formed into an annular shape. In addition to this, the sterilization device of Example 5 includes a structure in which the main emission direction of an LED element of the remaining one of the five light sources is directed toward the center of a bottom face portion of a sterilization target.

Comparative Example

The sterilization device of Comparative Example includes a structure in which only one light source is included, and the main emission direction of an LED element of the only one light source is directed toward the center of the bottom face portion (see FIG. 4).
(Performance Evaluation (Simulation))

Sterilization was performed using the sterilization devices of Examples 1 to 5 and the sterilization device of Comparative Example to simulate performance on ultraviolet light irradiation.

Performance evaluation on irradiation performance was conducted by measuring incoherent irradiance (hereinafter referred to as "irradiance") on each of cross-sections of the dented portion 12 and the protruded portion 14 forming the uneven shape 16 of the sterilization target 10. Note that output of the LED elements was set to 20 mW.

Furthermore, performance evaluation on sterilization performance was conducted by performing sterilization changing ultraviolet light irradiation methods in each of the sterilization devices of Examples 2 to 4.

Specifically, the time of ultraviolet light irradiation was set to five seconds, and "LRV/s" as a logarithmic reduction value (LRV) per unit time was calculated to conduct performance evaluation on sterilization performance.

First, an irradiation device including a plurality of LED elements for a single sterilization target was defined as a single irradiation unit. The plurality of LED elements included in each irradiation unit were arranged equidistantly and circumferentially with respect to the single sterilization target.

Figure 15:
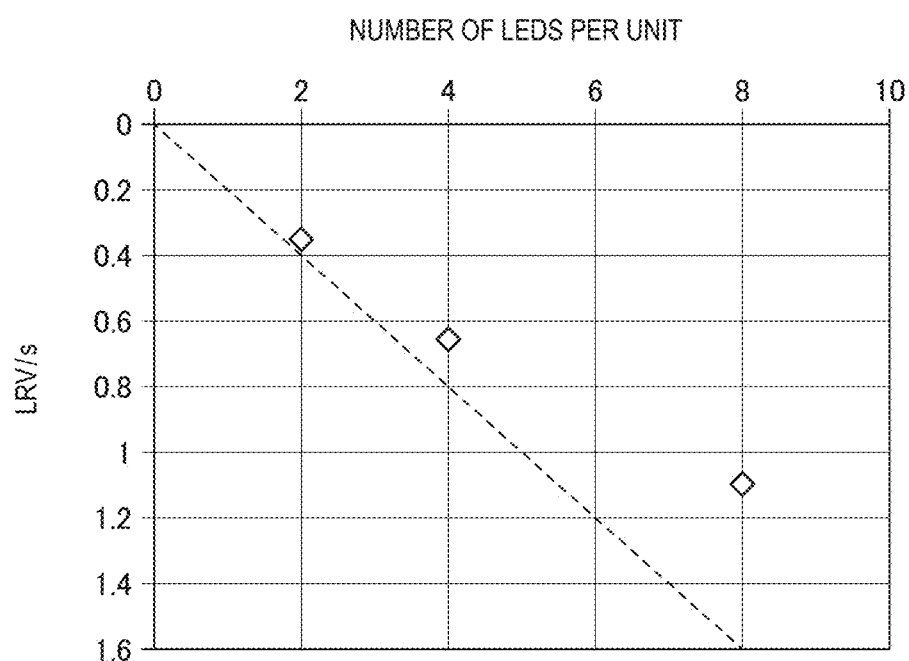
FIG. 15 is a graph representing a relationship between the number of LED elements included in a single irradiation unit and logarithmic reduction value per unit time in Examples of the present invention.

Then, the relationship between the number of the LED elements included in the single irradiation unit and the logarithmic reduction value per unit time was detected. FIG. 15 illustrates the detection results.

As illustrated in FIG. 15, it was confirmed that while sterilization performance improves as the number of the LED elements included in the single irradiation unit increases, the logarithmic reduction value per unit time is not proportional to the number of the LED elements. Note that, in FIG. 15, the horizontal axis represents the number of the LED elements included in the single irradiation unit (indicated as "NUMBER OF LED PER UNIT" in the drawing). Additionally, in FIG. 15, the vertical axis represents logarithmic reduction value per unit time (indicated as "LRV/s" in the drawing).

In other words, when a plurality of high output LED elements are arranged in a limited area, dissipation of heat from the LED elements is reduced, increasing junction temperatures of the LED elements, as a result of which output of the LED elements is reduced.

Then, when the irradiation device including a plurality of LED elements for a single sterilization target is defined as a single irradiation unit, the relationship between the number of the LED elements equidistantly and circumferentially arranged and the logarithmic reduction value per unit time (LRV/s) in the single irradiation unit indicates a proportionality coefficient of 1.0 or less.

Based on the results, performance evaluation on Examples 2 to 4 was conducted.

Evaluation of sterilization performance on the sterilization device of Example 2 was conducted by two kinds of measurements A1 and A2 as follows:

A1: measured irradiance when ultraviolet light was simultaneously applied from the four light sources.

A2: measured irradiance when ultraviolet light irradiation was performed in two stages by applying ultraviolet light at mutually different timings from two of the four light sources configured to apply ultraviolet light to two irradiation positions circumferentially not adjacent and from the remaining light sources.

Evaluation of sterilization performance on the sterilization device of Example 3 was conducted by two kinds of measurements B1 and B2 as follows:

B1: the six light sources were grouped into two sets: each set consisting of three light sources configured to apply ultraviolet light to three irradiation positions arranged at the apex angles of an equilateral triangle as seen from a bottom face of the sterilization target 10. Then, ultraviolet light was applied by the two sets of the light sources at mutually different timings to measure irradiance when ultraviolet light irradiation was performed in the two stages.

B2: the six light sources were grouped into three sets: each set consisting of two light sources configured to apply ultraviolet light to two irradiation positions arranged on a straight line passing through the center of the bottom face of the sterilization target 10. Then, ultraviolet light was applied by the three sets of the light sources at mutually different timings to measure irradiance when ultraviolet light irradiation was performed in the three stages.

Evaluation of sterilization performance on the sterilization device of Example 4 was conducted by three kinds of measurements C1, C2, and C3 as follows:

C1: measured irradiance when ultraviolet light was simultaneously applied from the eight light sources.

C2: measured irradiance when ultraviolet light irradiation was performed in two stages by applying ultraviolet light from the eight light sources at mutually different timings.

C3. measured irradiance when ultraviolet light irradiation was performed in four stages by applying ultraviolet light from the eight light sources at mutually different timings.

(Evaluation Results)
Irradiation Performance

As a result of the measurement of irradiance regarding the sterilization devices of Examples 1 to 5 and the sterilization device of Comparative Example, Examples 1 to 5 were confirmed to have higher irradiance onto the dented portion 12 than Comparative Example.

This verified that the sterilization devices of Examples 1 to 5 exhibited higher irradiation performance than the sterilization device of Comparative Example.

Sterilization Performance

As a result of the measurement of irradiance regarding the sterilization device of Example 2 by changing the ultraviolet light irradiation methods, the measurement of B1 showed an LRV/s of 0.65, and the measurement of B2 showed an LRV/s of 0.70.

As a result of the measurement of irradiance regarding the sterilization device of Example 3 by changing the ultraviolet light irradiation methods, the measurement of C1 showed an LRV/s of 0.90, and the measurement of C2 showed an LRV/s of 1.05.

As a result of the measurement of irradiance regarding the sterilization device of Example 4 by changing the ultraviolet light irradiation methods, the measurement of A1 showed an LRV/s of 1.1, the measurement of A2 showed an LRV/s of 1.30, and the measurement of A3 showed an LRV/s of 1.40.

(Verification of Multiple Stage Irradiation)

A one-time ultraviolet light irradiation time per sterilization target was set to one second, and simulation was conducted on the number of LED elements required to satisfy a logarithmic reduction value per unit time (LRV/s) of 3.

As a result, the structure in which a single irradiation unit included two LED elements required the number of LED elements corresponding to nine irradiation units, i.e., 18 LED elements.

In addition, the structure in which a single irradiation unit included four LED elements required the number of LED elements corresponding to five irradiation units, i.e., 20 LED elements.

Additionally, the structure in which a single irradiation unit included eight LED elements required the number of LED elements corresponding to three irradiation units, i.e., 24 LED elements.

Accordingly, it was confirmed that sterilization efficiency can be improved by arranging a plurality of irradiation units each including a small number of LED elements in the transfer direction of a sterilization target and allowing ultraviolet light to be applied from the LED elements in multiple stages.

This verified that the structure in which ultraviolet light irradiation is performed in multiple stages has higher sterilization performance than the structure in which ultraviolet light is simultaneously applied from all light sources included in a single irradiation unit.

Furthermore, it was verified that sterilization performance becomes higher as the number of stages for ultraviolet light irradiation is increased.

REFERENCE SIGNS LIST

1: Sterilization device
2: Moving unit
10: Sterilization target
10a: Cylindrical portion
10b: Bottom face portion
12: Dented portion
12a: First irradiation position
12b: Second irradiation position
12c: Third irradiation position
12d: Fourth irradiation position
14: Protruded portion
16: Uneven shape
20: Light source
22: LED element
30: Proximity sensor
40: Position controller
50: Irradiation controller
60: Irradiation unit
70: Light guide tube
80: Optical member
MR: Main emission direction
DL: Outline of region representing illumination distribution
LF: Light emitted vertically from LED element 22
SE: Region shaded by wall formed by protruded portion 14

The invention claimed is:

1. A sterilization method configured to apply ultraviolet light to a sterilization target that is a cap formed by a dented portion and a protruded portion from each of a plurality of light sources each including an LED element, the sterilization method comprising: transferring the sterilization target;

positioning the sterilization target; and irradiating the sterilization target with ultraviolet light,
  wherein, in the positioning, the sterilization target is stopped at a position in which ultraviolet light is emitted from the plurality of light sources; and
  wherein, in the irradiating, the sterilization target is irradiated a plurality of times with the ultraviolet light from at least one of the light sources arranged at a position where a maximum irradiation intensity of the ultraviolet light emitted from the light sources is applied to the dented portion of the target.

2. The sterilization method according to claim 1, wherein a plurality of irradiation units each including the plurality of light sources are arranged in a transfer direction of the sterilization target; and wherein each of the transferring, the positioning, and the irradiating is performed a plurality of times, and the plurality of times of the irradiating are performed at a plurality of different positions.

3. The sterilization method according to claim 2, wherein each of the LED elements of the plurality of light sources included in each of the irradiation units is arranged on a circumference of a perfect circle facing the sterilization target.

4. The sterilization method according to claim 2, wherein, in the positioning, the sterilization target is stopped at a position in which when the ultraviolet light is applied for one second from the LED elements of the plurality of light sources included in each of the irradiation units, an average dose to a bottom region of the dented portion is 0.1 mJ/cm$^2$ or more.

5. The sterilization method according to claim 1, wherein, in the irradiating, the ultraviolet light is applied to different positions on the sterilization target from the LED element of at least one of the plurality of light sources and the LED element of another one of the plurality of light sources.

6. The sterilization method according to claim 1, wherein a plurality of irradiation units each including the plurality of light sources are arranged in the transfer direction of sterilization targets each being the sterilization target at the same interval as an interval between the sterilization targets that are adjacent to each other, and when the sterilization targets move to previously set irradiation positions, the ultraviolet light is simultaneously applied to the sterilization targets at the irradiation positions from the plurality of light sources included in the plurality of irradiation units.

7. The sterilization method according to claim 1, wherein, as the ultraviolet light, ultraviolet C wave is applied.

8. The sterilization method according to claim 1, wherein the sterilization target is a cap configured to close an opening portion of a container for accommodating an article.

9. The sterilization method according to claim 8, wherein the cap includes a cylindrical portion having one end closed at a bottom face portion and the other end open;
  wherein the protruded portion is an annular protrusion formed at a position spaced by a gap from an inner diameter surface of the cylindrical portion on the bottom face portion; and wherein the dented portion is an annular groove formed between the inner diameter surface and the protruded portion on the bottom face portion.

10. The sterilization method according to claim 9, wherein the plurality of light sources are arranged to be equidistantly spaced apart from each other along a circle facing the annular groove, and the ultraviolet light is applied to the annular groove from the plurality of light sources.

11. The sterilization method according to claim 2, wherein, in the irradiating, the ultraviolet light is applied to different positions on the sterilization target from the LED element of at least one of the plurality of light sources and the LED element of another one of the plurality of light sources.

12. The sterilization method according to claim 1, wherein a plurality of irradiation units each including the plurality of light sources are arranged at an interval that is the same interval as an interval between a plurality of said sterilization targets that are adjacent to each other in a transfer direction, and when the sterilization targets move to previously set irradiation positions, the ultraviolet light is simultaneously applied to the sterilization targets at the irradiation positions from the plurality of light sources included in the plurality of irradiation units.

13. The sterilization method according to claim 2, wherein, as the ultraviolet light, ultraviolet C wave is applied.

14. The sterilization method according to claim 2, wherein the sterilization target is a cap configured to close an opening portion of a container for accommodating an article.

* * * * *